United States Patent [19]
Baer et al.

[11] Patent Number: 5,547,849
[45] Date of Patent: Aug. 20, 1996

[54] APPARATUS AND METHOD FOR VOLUMETRIC CAPILLARY CYTOMETRY

[75] Inventors: Thomas M. Baer; Louis J. Dietz, both of Mountain View; Robert S. Dubrow, San Carlos; Paul G. Hayter, Los Altos; Michael Hodges, Palo Alto; Bala S. Manian, Los Altos Hills; Robert J. Shartle, Livermore, all of Calif.

[73] Assignee: Biometric Imaging, Inc., Mountain View, Calif.

[21] Appl. No.: 236,342

[22] Filed: May 2, 1994

Related U.S. Application Data

[63] Continuation-in-part of Ser. No. 18,762, Feb. 17, 1993, abandoned.

[51] Int. Cl.[6] ............................................. G01N 33/536
[52] U.S. Cl. .................. 435/7.24; 435/7.21; 435/287.2; 435/288.7
[58] Field of Search ...................................... 356/244, 246, 356/427; 382/128, 133, 134; 250/432 R, 459.1, 458.1, 461.1, 461.2; 435/7.2, 7.21, 7.1, 7.22, 7.23, 7.24, 7.25, 287.2, 288.7; 422/50, 55, 57–59, 68.1, 73, 82.05

[56] References Cited

U.S. PATENT DOCUMENTS

| | | | |
|---|---|---|---|
| 2,850,239 | 9/1958 | Polanyi et al. | |
| 3,777,283 | 12/1973 | Elkins | 356/246 |
| 3,918,812 | 11/1975 | Holm | 356/73 |
| 4,284,412 | 8/1981 | Hansen et al. | 23/230 B |
| 4,284,897 | 8/1981 | Sawamura et al. | 250/461 B |
| 4,318,886 | 3/1982 | Kawahara et al. | 422/82.05 |
| 4,665,553 | 5/1987 | Gershman et al. | 382/6 |
| 4,683,579 | 7/1987 | Wardlaw . | |
| 4,727,020 | 2/1988 | Recktenwald | 435/6 |
| 4,758,727 | 7/1988 | Tomei et al. | 250/458.1 |
| 4,877,966 | 10/1989 | Tomei et al. | 250/458.1 |
| 4,979,824 | 12/1990 | Mathies et al. | 356/318 |
| 5,037,207 | 8/1991 | Tomei et al. | 356/444 |
| 5,072,382 | 12/1991 | Kamentsky | 364/413.08 |
| 5,091,652 | 2/1992 | Mathies et al. | 250/58.1 |
| 5,107,422 | 4/1992 | Kamentsky et al. | 364/413.08 |
| 5,117,466 | 5/1992 | Buican et al. | 382/6 |
| 5,127,730 | 7/1992 | Brelje et al. | 356/318 |
| 5,274,240 | 12/1993 | Mathies et al. | 250/458.1 |

FOREIGN PATENT DOCUMENTS

0266881A3  11/1988  European Pat. Off. .

OTHER PUBLICATIONS

Kamentsky. Cytometry, 12:381–387 (1991).
Haugland. Handbook of Fluorescent Probes and Research Chemicals, 5th Ed. (1992) pp. 221, 223.
Burger, Douglas et al., "Acouto–Optic Laser–Scanning Cytometer", *Cytometry*, vol. 9 (1988), pp. 101–110.
Landay, Alan et al., "Application of flow cytometry to the study of HIV infection", *Aids*, vol. 4 (1990), pp. 479–497.
Mroz, Edmund A. et al., "Fluorescence Analysis of Picoliter Samples", *Analytical Biochemistry*, vol. 102 (1980), pp. 90–96.

Primary Examiner—James C. Housel
Assistant Examiner—Gary Tanigawa
Attorney, Agent, or Firm—Fulwider Patton Lee & Utecht

[57] ABSTRACT

The apparatus and method of the present invention disclose a scanning imaging cytometer wherein an unprocessed biological fluid sample is reacted with a fluorescently-labeled binding agent. The reacted sample undergoes minimal processing before it is placed into a capillary tube. The sample is optically scanned and fluorescence excitation is recorded from a plurality of columnar regions of the capillary tube, each columnar region generally defined by the spot size of the excitation beam and the depth dimension of the capillary tube. A spatial filter of a sufficient pinhole diameter is selected to allow simultaneous volumetric detection of all fluorescent targets in each columnar region.

47 Claims, 3 Drawing Sheets

APPARATUS AND METHOD FOR VOLUMETRIC CAPILLARY CYTOMETRY

CROSS-REFERENCE TO RELATED APPLICATIONS

This is a continuation-in-part of U.S. Ser. No. 08/018,762 now abandoned. The present application is also related to U.S. patent application entitled "Method and Apparatus for Cell Counting and Cell Classification" invented by Ning L Sitzo and Louis J Dietz, U.S. Ser. No. 08/236,645, filed May 2, 1994, pending and owned by the same Assignee. The related application is incorporated by reference as if fully set forth herein.

TECHNICAL FIELD

This invention relates to automated cytometry instruments and procedures and to the identification and enumeration of cellular components of biological fluids.

BACKGROUND ART

Rapid identification and enumeration of the various components of biological fluids is an important research and diagnostic aim. Minimal processing and handling of samples would contribute to the widespread use of such techniques.

In the case of enumeration of leukocyte subclasses of human blood, the need for improved techniques is especially keen. For example, the usefulness of monitoring CD4+ lymphocyte levels in noting the progression from HIV positive status to AIDS has underscored the need for a fast, inexpensive, and reliable method to analyze patient blood samples.

Landay et al., "Application of flow cytometry to the study of HIV infection," AIDS 4:479–497 (1990) describes the utility of a technique in understanding the biology of HIV infection. Multiple-color flow cytometric analysis can be applied to the study of HIV disease by using various monoclonal antibodies to perform phenotypic analysis of blood samples. This technique is also useful in other immune system determinations, as in evaluating the status of organ transplant or leukemia patients.

Flow cytometry is a well-known technique wherein cells may be characterized and separated based on fluorescent emission. A labeled, mono-dispersed cell suspension travels through a tube in a fine fluid stream and is presented to an excitation beam. The emitted fluorescence of each cell is measured by appropriate detectors and the cells may be split into droplets and sorted according to given parameters by electrical and mechanical means.

Flow cytometry may be used to identify and enumerate specific subclasses of blood cells. For example, in U.S. Pat. No. 4,284,412 Hansen et al., lymphocytes which have been reacted with fluorescently-labeled monoclonal antibodies are separated from red blood cells and presented one by one to a fixed detector in a flow cytometry system. Each cell is characterized by analysis of forward light scatter, right angle scatter, and fluorescence. This method requires complex sample preparation and instrumentation. While flow cytometry has improved assay reliability and reproducibility in this application, it generally cannot directly provide absolute cell counts for lymphocyte subsets. Independent white blood counts and differential white counts are required to calculate absolute cell counts per Unit volume. In the usual flow cytometry practice, in order to distinguish lymphocytes from monocytes and granulocytes, a lymphocyte gate based on forward and side light scatter patterns must be established for each sample.

Flow cytometry is not routinely used for identifying and enumerating lymphocyte subclasses in the presence of red blood cells, although U.S. Pat. No. 4,727,020 Recktenwald provides a contrary example. Removal of the red blood cells, by density-gradient separation or lysing, increases the time, cost and number of blood-handling steps per assay. Additional blood-handling steps increase the potential for exposure to bloodborne infectious agents. As stated above, the resultant data produced by the flow cytometry method is inadequate for some purposes. In order to calculate absolute cell count per unit volume, flow cytometric data must generally be combined with additional data obtained from other methods. Also, because flow cytometers conventionally utilize a fluid stream passing through a small nozzle, they may generate aerosols which pose an additional source of biohazardous materials for laboratory personnel.

An alternative is to fix sample position relative to the excitation beam. For example, in U.S. Pat. No. 4,758,727 and its divisional, U.S. Pat. No. 4,877,966, Tomei et al., a method and apparatus for measurement of low-level laser-induced fluorescence is described. In this invention, a coherent laser beam is passed through a three-dimensional scanner and focused onto a static target. The target is an object such as a monolayer cell culture or tissue section. A beam spot, having a size as small as one micron, is passed back and forth across the target by a scanner whose path and movement rate are computer-controlled. Fluorescent light is gathered by a biased-cut fiberoptic base plate and relayed to a detector positioned on the opposite side of the target from the beam.

U.S. Pat. No. 5,037,207, also granted to Tomei et al., discloses a laser imaging system with enhanced spatial resolution and light gathering efficiency which allows for digital imaging of a target of varying size, dependent upon the data retrieval and storage limitations of the supporting computer system. The system utilizes a novel optical fiber detector assembly and a rapid scan for collection of all light from every laser spot to create a quantitative digital reproduction of the image on the surface of a target.

U.S. Pat. Nos. 5,072,382, Kamentsky, and 5,107,422, Kamentsky et al., disclose an apparatus and method for scanning a cell population with a beam to generate multi-parameter optical data based on each cell's specific location. The scan is made of a surface on which cells have been deposited. A background level is estimated for the neighborhood surrounding each cell based on digital data and corrections are made for the background level.

In "Acousto-Optic Laser-Scanning Cytometer," *Cytometry* 9:101–110 (1988) Burger and Gershman and U.S. Pat. No. 4,665,553 Gershman et al., a laser-scanning cytometer is disclosed. An optical scan is made of a lysed and washed sample in a cuvette by a Bragg cell-controlled scanner. The cuvette is translated in a stepwise fashion in one direction relative to the scanner. The scanner operates in a direction perpendicular to the direction of cuvette translation and the scan occurs along the side of the cuvette. Once a cell is located, a beam optimization algorithm operates to steady the beam on the cell and measurements of forward light scatter, orthogonal light scatter, and fluorescence are made. Then the process is repeated.

In U.S. Pat. No. 5,117,466, Buican et al., describe a fluorescence analysis system in which data from a flow cytometer establish identification criteria used by a confocal laser microscope to virtually sort the cellular components of a sample. Birefringent optics and Fourier-Transform technology are used to visually select and display cells or subcellular structures having the desired spectral properties.

In "Fluorescence Analysis of Picoliter Samples," *Analytical Biochemistry* 102:90–96 (1980) Mroz and Lechene teach a method of handling picoliter-volume samples to gather fluorescence intensity data. Samples are taken up via syringe in a single siliconized capillary tube with oil between the samples. Measurements are made of an optical fluorescence chamber defined by a pinhole diaphragm, a microscope objective, and the diameter of the capillary tube.

U.S. patents granted to Mathies et al. are also relevant to the field of the present invention. In U.S. Pat. No. 4,979,824, a high sensitivity detection apparatus is described. This apparatus is based on a flow cytometry system and utilizes a spatial filter to define a small probe volume that allows for detection of individual fluorescent particles and molecules. Laser power and exposure time of the sample are chosen for the best signal-to-noise ratio. Real-time detection of photon bursts from fluorescent particles is used to distinguish the number, location or concentration of the particles from background energy.

In U.S. Pat. No. 5,091,652 Mathies et al., a laser-excited fluorescent scanner is revealed for scanning separated samples using a confocal microscope. The sample is preferably separated by and detected from an electrophoresed slab gel, but may also be on a membrane, filter paper, petri dish, or glass substrate. The confocal microscope forms an illumination volume in the gel and the beam is oriented so that background scattering is minimized by the polarization characteristics of the scattered light.

U.S. Pat. No. 5,274,240 also granted to Mathies et al. and a continuation-in-part of the above patent, teaches a laser-excited capillary array scanner. This invention is primarily intended for fluorescence detection from an array of capillary tubes containing samples that have been separated by capillary electrophoresis. The fluorescence detection assembly employs a confocal system to detect fluorescence from the interior volumes of each capillary tube.

The current cytometry art generally requires time-consuming and potentially hazardous sample-handling and component separation steps. It fails to allow for rapid volumetric identification and enumeration of sub-populations of a cell suspension that are present within a mixed population. The techniques of the prior art often require trained personnel.

It is therefore an object of the present invention to provide a quick, simple to use, less expensive, safer, automated apparatus and method for directly obtaining counts of specific cellular subsets in biological fluids in a volumetric manner and which require small volumes of sample and reagent.

SUMMARY OF THE INVENTION

The above object has been achieved with an apparatus and method for identifying and enumerating the cellular components of a biological fluid in a volumetric manner based on the formation of fluorescent complexes and the optical scanning of a capillary tube containing the sample in a static and minimally processed form. The fluorescence is detected from throughout a non-flowing cell suspension and enumeration may be done in a precise volume for the purpose of obtaining absolute cell counts. "Absolute" as defined herein, means the absolute number of cells per volume as represented by the volume scanned. As defined herein, "cell" means a whole cell or a part of a cell. The complexes are the result of a reaction between fluorescently-labeled binding agents and corresponding binding sites present in the cellular components of the fluid. An excitation laser beam is directed by an optical scanner to a columnar region of the capillary tube, the columnar region generally defined by the interior depth dimension of the capillary tube and the beam spot of the laser. A spatial filter of sufficient pinhole aperture is chosen to selectively detect the fluorescence emitted throughout the columnar region and is disposed between the capillary tube and a detection means. Because no separation of bound and unbound fluorescently-labeled binding agent is necessary in the sample, both are viewed as fluorescence by the detection means. However, areas of heightened fluorescence intensity occur where the labeled binding agents congregate, namely on the binding sites present in the cellular components of the sample. The detection means, therefore, records a signal of heightened fluorescence intensity above a given threshold of background fluorescence as corresponding to a single cell.

In the preferred embodiment, a laser creates an excitation beam of a wavelength of 600 to 1000 nanometers and is focused onto a capillary tube of rectangular cross-section from a position directly above the capillary tube. The spot size of the laser beam at the point of its intersection with the capillary tube is 5 to 15 microns in diameter, depending upon the expected cell size, and the illuminated depth dimension of the capillary tube is 25 to 225 microns. As described later, there is a relationship between the spot size and the capillary tube depth dimension. In the present invention, an excitation beam is scanned in two directions to impinge upon the outer wall of a transparent capillary tube that is in a fixed position. The first scan direction follows a path transverse to the longitudinal axis of the capillary tube, i.e. the wide portion of the rectangular cross-section of the capillary tube, and begins and ends at points that are beyond the lateral boundaries of the capillary tube. The second scan direction follows a path along the longitudinal axis of the capillary tube. The scan of a known volume of the capillary tube, achieved by measuring the beginning and ending points in the second scan direction, or by beginning and ending the scan at defined points, can be used to calculate the presence of a particular Subpopulation of cellular components per unit volume, since the cross-sectional area of the capillary tube is known.

The apparatus of the present invention is especially well-suited to the detection of sub-classes of blood cells. In a typical assay, a sample of whole uncoagulated blood is obtained and incubated with an excess amount of fluorescently-labeled antibodies that are directed toward various cell surface markers present on blood cell subclasses. The fluorophores are chosen so that they will activate in the wavelength range of the excitation beam. This wavelength range has also been specifically selected to minimize interference due to autofluorescence from blood components not of interest. The sample containing fluorescently-labeled antibody in both complexed and free form is generally diluted and then inserted into the capillary tube. The tube is then optically scanned at wavelengths necessary to excite the fluorophores. Based on fluorescent emission from specific fluorophores used to label specific antibodies, the number of cells of a certain type per unit volume can be quickly determined, as can ratios of cell types present in the blood or other biological fluid sample.

The instrument and technique of the present invention quickly detect cellular components of biological fluids in a precise volume and require minimal processing of the sample. The present invention substantially cuts down on assay times and costs and requires minimal handling of samples, an especially important precaution during the examination of blood samples. Because no special instruments are necessary for processing the samples and the number of requisite reagents is kept to a minimum, the present invention is well-adapted for use in a clinical setting.

BEST MODE FOR CARRYING OUT THE INVENTION

Figure 1:
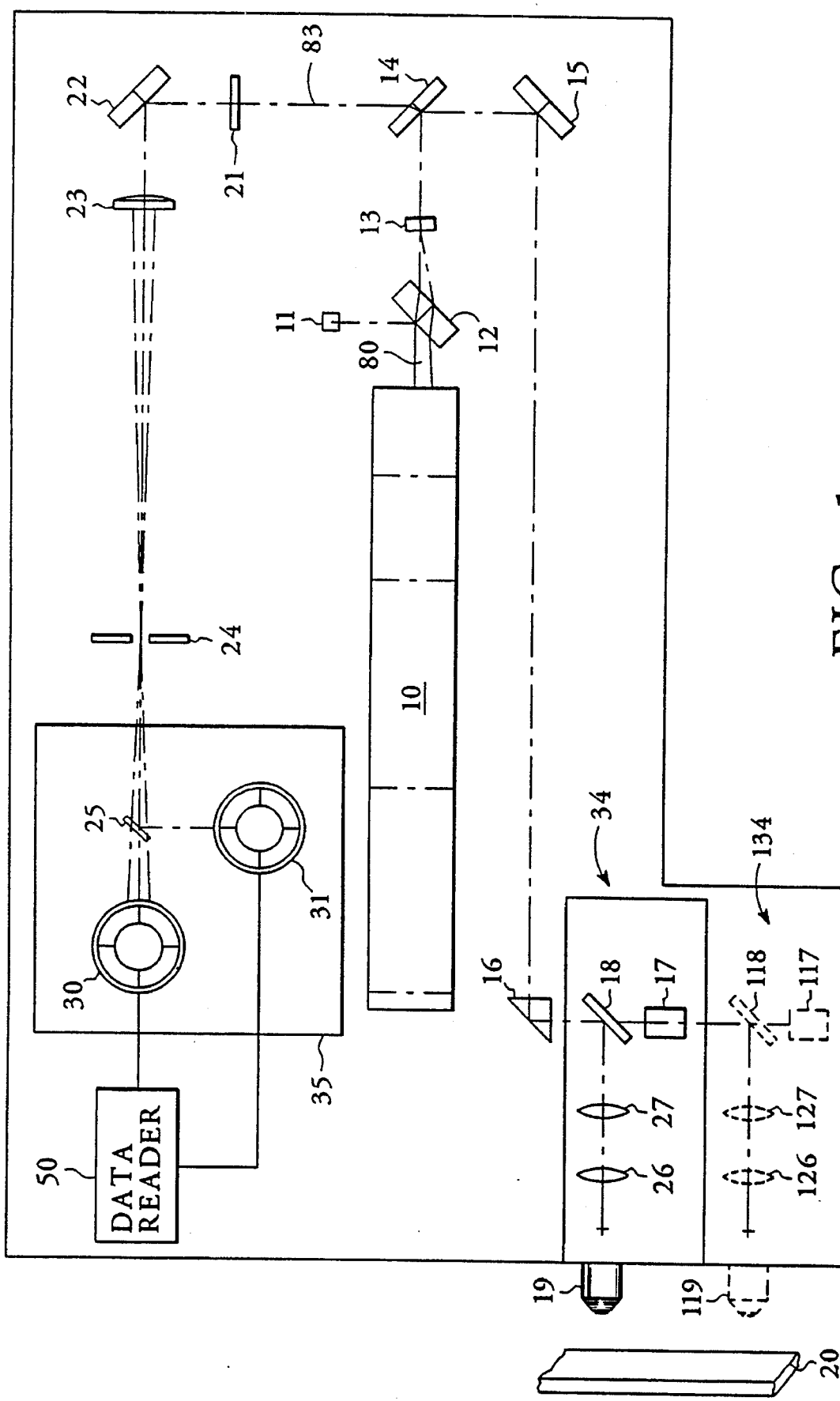
FIG. 1 is a plan view of an apparatus according to the present invention.

With reference to FIG. 1, laser 10 generates an excitation beam 80 that passes first through glass plate 12 which optically communicates with power monitor 11, then through laser line filter 13 and through spectral dispersion means 14 which acts as a mirror for the selected laser beam wavelength. The spectral dispersion device may be, for example, a dichroic beam splitter, a prism, or a grating. The excitation beam is then directed to mirror 15 and through right angle prism 16 to scan assembly 34. In FIG. 1, scan assembly 34 comprises a galvanometer 17 with attached galvo mirror 18, lenses 26 and 27, and lens 19. Alternatively, the scan assembly may comprise a multifaceted polygonal mirror. The excitation beam 80 of the present invention impinges upon galvo mirror 18 which continually changes position because it is in communication with galvanometer 17 thereby causing a change of position of the excitation beam. Within scan assembly 34, the excitation beam travels from the galvo mirror 18 through lens 27 then through lens 26. From lens 26, the excitation beam is directed through lens 19 so that a focal spot of the beam may impinge upon the outer wall of a transparent capillary tube 20.

The excitation beam impinging upon the outer wall traverses the wall and illuminates a columnar region of the sample causing fluorescent emission from the sample. Light collection occurs in an epi-illumination manner. The emitted fluorescence is collected by lens 19 and directed back, as retrobeam 83, through scan assembly 34. Lens 19, seen in FIG. 2, has a central portion for passage of incident beam 80 and uniform depth of focus of incident beam 80 through capillary tube 20. Because fluorescent emission is over a very wide angle, represented by rays 32a and 32b, fluorescent collection occurs over a wider portion of objective 19. Returning to FIG. 1, the retrobeam 83 travels from scan assembly 34 to right angle prism 16 to mirror 15 and spectral dispersion device 14. Due to its fluorescence emission wavelength, retrobeam 83 is transmitted through spectral dispersion device 14 and through bandpass filter 21 to mirror 22 where it is directed through collimating lens 23. The retrobeam is then selectively passed through spatial filter 24 and into the detection means 35. The spatial filter 24 has a predetermined pinhole aperture of a diameter that permits passage of only that fluorescence emission from a region defined by the illuminated segment within the capillary tube.

Detection means 35 comprises a detection channel such as detector 30 which reads the fluorescent signal of the retrobeam 83 and is in communication with data reader 50 which converts it from analog to digital form. The detector is a light measuring device such as a photo-multiplier tube or photodiode. The signal is recorded by data reader 50 as a unit of fluorescence intensity. The detection means 35 may contain any number of detection channels. For instance, a spectral dispersion device 25 is positioned between spatial filter 24 and detectors 30 and 31 in FIG. 1 to separate the wavelengths of the fluorescent emission of the sample and to selectively direct light of one wavelength to one detector and light of a second wavelength to a second detector. In this manner, multiple spectral dispersion devices and multiple detectors may be incorporated into the detection means for detection of fluorescence at different wavelengths from multiple fluorophores. In a similar manner, multiple lasers may be utilized for excitation of the sample at different wavelengths.

Figure 2:
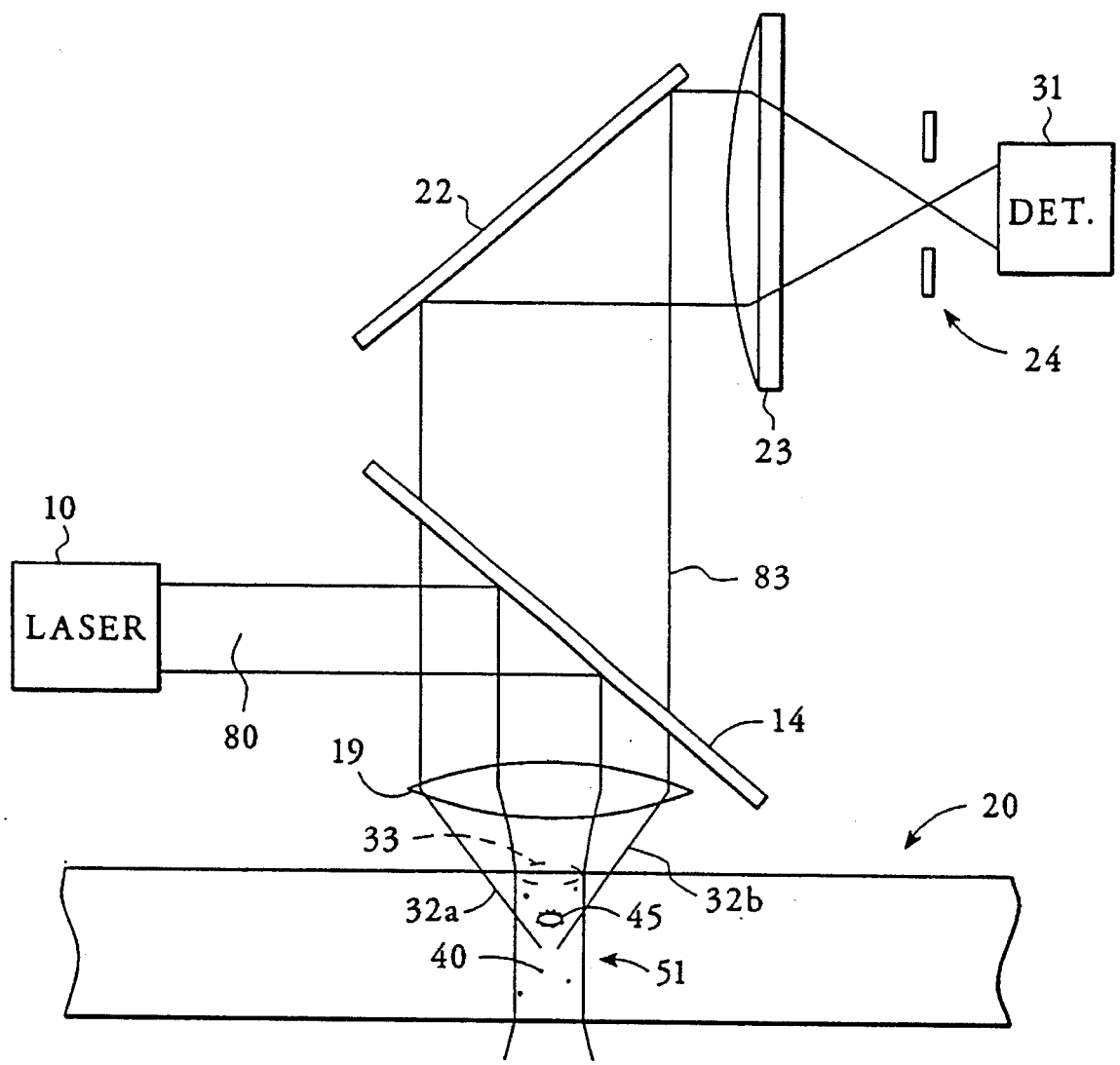
FIG. 2 is a side view of a sample-filled capillary tube according to the present invention, illustrating an illuminated columnar region, and both excitation and emission beams.

A critical feature of the present invention is illustrated in FIG. 2. Spatial filter 24 is selected with a pinhole aperture that collects light over a large numerical aperture, but confines the depth of detection to the interior depth dimension of the capillary tube. The spot size of excitation laser beam 80 on the outside wall of capillary tube 20 is of a generally constant diameter, and has been chosen to provide uniform illumination along the depth dimension of the capillary tube. Thus, the present invention relies upon a dependent relation of the spot size of the excitation beam, the depth dimension of the capillary tube, and the pinhole aperture of the spatial filter.

Figure 3:
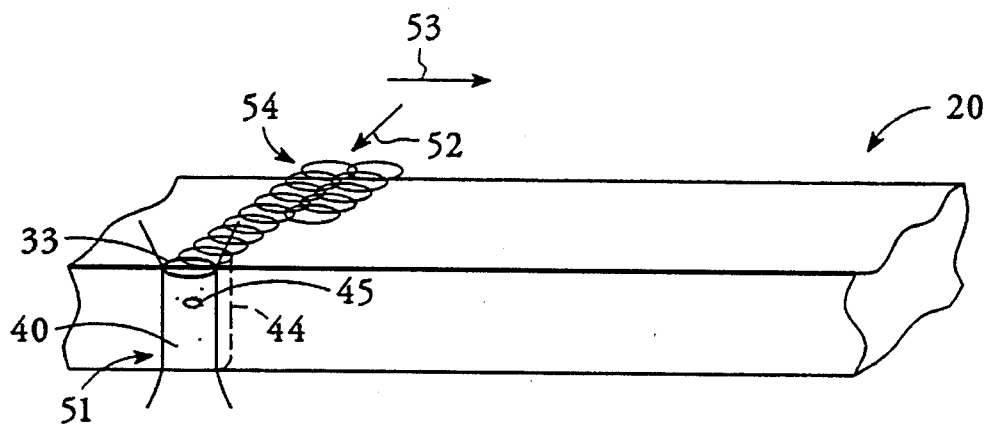
FIG. 3 is a perspective view of a sample-filled capillary tube showing overlapping beam spots and an illuminated columnar region according to the present invention.

The capillary tube 20 is a transparent sample holder of known dimensions. The capillary tube preferably has a rectangular cross-section with a shorter dimension defining an interior depth of 25 to 225 microns and a longer dimension defining a width of 1 millimeter. The length of the capillary tube is not as critical, but the beginning and ending points of the scan in a direction along the length of the capillary tube define the precise volume of the segment scanned. In the present invention, a capillary tube length of 40 millimeters has generally been used. The capillary tube is fixedly positioned directly below the excitation beam so that the scan of the capillary tube occurs in a top-down manner. The intersection of the excitation beam and the capillary tube is generally defined by columnar region 51, as shown in FIGS. 2 and 3. The top dimension of the columnar region is circular beam spot 33 of 5 to 15 microns. The size of the beam spot is chosen so that the entire depth dimension of the capillary tube is illuminated.

Figure 4:
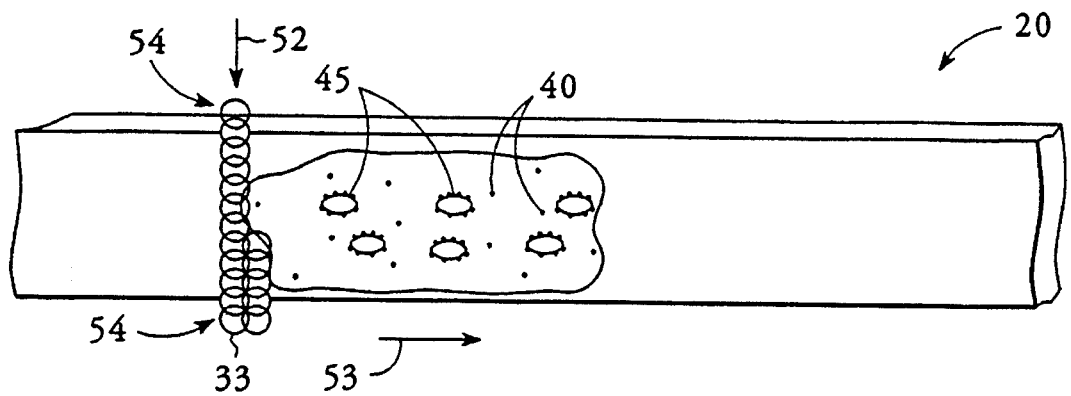
FIG. 4 is a top view of a sample-filled capillary tube, showing overlapping beam spots according to the present invention.

After a columnar region of the capillary tube is illuminated and the fluorescence emitted from its contents is detected and recorded, the optical scanning means is moved to a new position to illuminate a new columnar region. The movement is of an amount that is only a fraction of the beam spot size, so that each illuminated columnar region 51 partially overlaps another such region 44, as in FIG. 3. The optical scanning means continues in this manner of illuminating and fluorescently exciting a region from which fluorescent emission is detected and recorded, then is moved slightly to illuminate a new columnar region and to repeat the process. In the preferred embodiment, the optical scanning means follows a scan path in one direction indicated by arrow 52 that is transverse to the longitudinal axis of the capillary 10 tube, i.e. along its width, and in the other direction along the length of the capillary tube, indicated by arrow 53, to form a two-dimensional array of beam spots. In FIG. 1, the dashed lines 134 indicate a change of position of scan assembly 34, so that dashed galvanometer 117 and dashed galvo mirror 118 represent galvanometer 17 and galvo mirror 18 in altered positions. In the same manner, dashed lenses 127, 126 and 119 represent lenses 27, 26, and 19 in altered positions. As shown in FIGS. 3 and 4, the transverse scan begins and ends at points 54 beyond the lateral boundaries of the capillary tube. This overscan is effective in identifying edge anomalies of the capillary tube.

Figure 5:
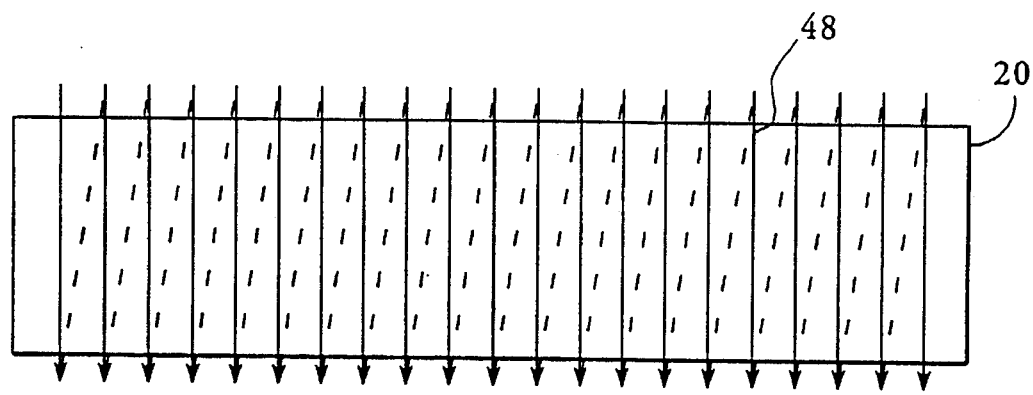
FIG. 5 is a schematic representation of the optical scanning path according to a preferred embodiment of the present invention.

FIG. 5 shows a schematic representation of scan path 48 from above capillary tube 20, according to the preferred embodiment of the present invention. The excitation beam spots are moved along the scan path in a transverse direction, then snapped back to follow a closely-spaced parallel path also in the transverse direction. The process is repeated continually so that the scan also covers a segment along the longitudinal axis of the capillary tube. In this manner, fluorescence emission occurs and is detected from any chosen length of the capillary tube.

The method disclosed in the present invention allows for analysis of a sample of biological fluid with a minimum of preparation. According to the present invention, a biological fluid is incubated with an excess amount of a binding agent that contains a fluorophore of known optical characteristics. The fluorescently-labeled binding agent is selected to react with binding sites present within the sample. For example, a fluorescently-labeled antibody directed to an antigen present on some cellular component of the biological fluid may be added to the sample. The labeled binding agents and the binding sites form fluorescent complexes that will emit a signal when used with the apparatus of the present invention.

After the sample is incubated with the labeled binding agent, it is diluted, if necessary, and then placed directly into capillary tube 20. No lysing of components of the biological fluid nor separation of bound and unbound binding agent is required at any point in the practice of the method of the present invention. An optical scan is made of the sample in a volumetric manner and fluorescence emission is sequentially recorded from each illuminated columnar region.

The enumeration may occur in an absolute volume, depending on the desired application, by noting the beginning and ending points of the lengthwise scan of the capillary tube and measuring the distance scanned or by scanning between specific identification marks on the capillary tube. This quantitation of all of the fluorescent targets in a fixed, precise volume is a powerful method of quickly obtaining detailed population data. This volume is fixed by using a uniform cross-sectional area capillary tube or by independently measuring the volume of the capillary tube between specific identification marks. Alternatively, a ratio can be obtained without counting a precise volume, but rather by comparing relative counts of different components of the sample.

Figure 6:
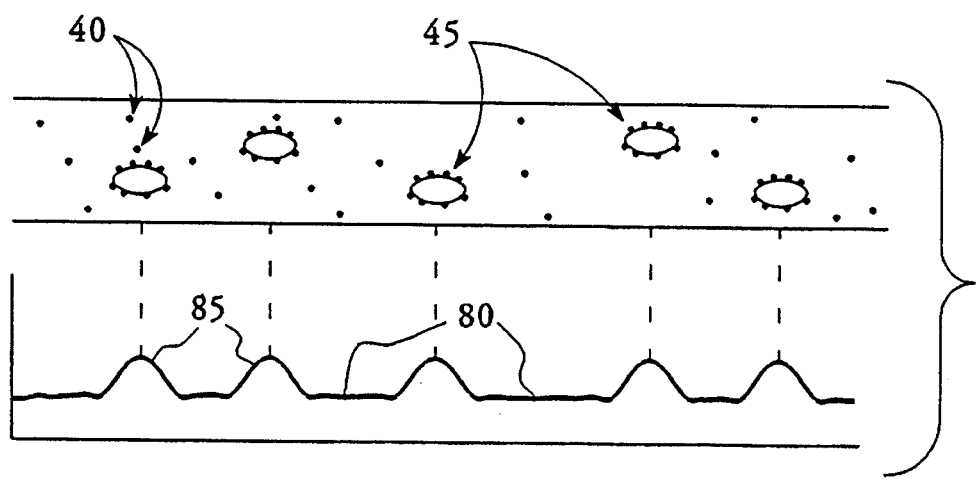
FIG. 6 is a schematic representation of a labeled cell suspension and the corresponding detector signal.

Data reader 50, in FIG. 1, records events, i.e. an increase above the background level of fluorescence exceeding some threshold value, as shown in FIG. 6. The events correspond to the occurrences of cells of a particular type in the sample. Fluorescence emission occurs from both the binding agent-binding site complexes 45 and from the free binding agent 40, but a more intense signal 85 relative to background level 80 comes from areas where the binding agent is clustered, i.e. cells exhibiting binding sites to which the binding agent is directed. Therefore, a signal of heightened fluorescence 85 corresponds to a cell, linked by dashed lines in FIG. 6, and is recorded as such.

The method of the present invention does not require removal of unreacted fluorescently-labeled binding agent. Dilution of the sample before optical scanning serves to improve signal to noise ratios so that fluorescent imaging according to the present invention occurs in a quick manner with minimal processing steps. Dilution also serves to minimize the occurrence of cell overlap in the sample. In the practice of this invention, optimal results are obtained when the cells of the sample are on the order of 10 microns in size and the cell density is less than 5000 per microliter.

An example of this method's utility is illustrated by an assay for the determination of leukocyte subclasses present in a blood sample. In a typical assay, a sample of whole uncoagulated blood is incubated with fluorescently-labeled antibodies that are directed to specific cell surface markers. For example, anti-CD4 and anti-CD8 labeled with fluorophores having different optical characteristics may be incubated with the whole blood sample. Within the sample, the leukocytes that bear either CD4 or CD8 or both cell surface markers will react with the labeled antibodies to form fluorescent complexes. After a sufficient reaction time, the whole blood sample is diluted and inserted into a capillary tube. The capillary tube is then optically scanned according to the present invention. The wavelength range of the optical scan is selected so as to activate the fluorophores being used and to minimize interference due to autofluorescence from blood components not of interest. Fluorescent emission corresponding to the fluorophores that were used to label the anti-CD4 and anti-CD8 are detected and recorded. The presence of leukocytes bearing either or both of the cell surface markers to which these antibodies are directed is then enumerated. Results may be presented as an absolute cell count per unit volume, by counting the number of cells of a certain subclass present within a given volume, the volume being determined by the length of the scan and the cross-sectional area of the capillary tube. Results may also be presented as ratios, e.g. CD4/CD8 leukocyte ratios, by counting the number of cells bearing each of these cell surface markers and comparing the two. The usefulness of this last illustration is readily evident, as this ratio is important in determining the progression of AIDS.

When an assay is performed to determine leukocyte subclasses in whole uncoagulated blood using the technique of the present invention, a two or three minute wait between placement of the reacted sample into the capillary tube and the optical scan allows for the natural density of the numerous red blood cells present in the sample to cause settling of the red blood cells to the bottom of the capillary tube and the subsequent displacement of the white blood cells. This natural buoyancy effect causes a resultant location of the white blood cells near the upper portion of the capillary tube and assists in fluorescence detection because of the top-down scan geometry of the present invention.

As in the above example, fluorophores with different optical characteristics can be combined with binding agents directed to different binding sites, so that the presence of multiple reaction moieties in the sample can be detected. From the precise known volume of the capillary tube that has been scanned, a quick reading will identify the number of cells of a particular subclass per unit volume that are present in the sample. The optical system is simply set to excite each fluorophore at its crucial wavelength and a detection channel is created to correspond to the emission wavelength of each fluorophore.

The apparatus and method of the present invention are suited to many applications, including those requiring absolute counts within a known volume. For example, cell kinetics studies, cell toxicity studies using intercalating dyes, and in situ hybridization may be adapted for analysis according to the present invention. In addition, the volumetric method of the present invention allows for the avoidance of artifacts that may be present when immunological and other biochemical responses are studied in cells located on a surface rather than in a cell suspension. Although the cells are detected from within a capillary tube, the present invention presents the sample in a manner that allows for flow cytometric-type analysis on relatively stationary localized cells. Therefore, the cells may be detected in a location-specific manner or be identified for subsequent visual examination.

We claim:

1. A method of identifying and enumerating cellular components of biological fluids via fluorescence, the method comprising:

obtaining a sample of biological fluid having cellular components;

incubating the sample with an excess amount of a fluorescently-labeled binding agent directed to binding sites present on the cellular components to form fluorescent complexes;

placing the sample into a capillary tube, the capillary tube having specified dimensions and a longitudinal axis;

optically scanning the sample with an incident beam of light having a wavelength selected to excite the fluorescent complexes, so as to sequentially intersect the capillary tube in a plurality of beam spots of specified diameter to illuminate a plurality of columnar regions;

sequentially detecting emitted fluorescence confined to an interior depth dimension of each columnar region;

recording the emitted fluorescence from each columnar region of heightened fluorescence intensity; and enumerating the cellular component of the sample from the emitted fluorescence.

2. A method as in claim 1, further comprising diluting the sample after said incubating step and prior to said placing the sample into a capillary tube step.

3. A method as in claim 1 wherein optically scanning the sample comprises intersecting a horizontally positioned capillary tube with an incident beam positioned directly above the capillary tube.

4. A method as in claim 1 wherein optically scanning the sample comprises scanning with an incident beam of a wavelength of 600 to 1000 nanometers.

5. A method as in claim 1 wherein reacting the sample with a fluorescently-labeled binding agent comprises using a binding agent labeled with a fluorophore that is activated at an excitation wavelength in the range of 600 to 1000 nanometers.

6. A method as in claim 1 wherein optically scanning the sample comprises scanning with an incident beam that is 5 to 15 microns in diameter at an intersection of the incident beam and the capillary tube.

7. A method as in claim 1 wherein placing the sample in a capillary tube comprises placing the sample in a capillary tube of rectangular cross-section with a shorter dimension of the cross-section defining a depth of the capillary tube and a longer dimension of the cross-section defining a width of the capillary tube.

8. A method as in claim 1 wherein placing the sample in a capillary tube comprises placing the sample in a capillary tube having a depth dimension of 25 to 225 microns.

9. A method as in claim 1 wherein optically scanning the sample comprises traversing a path in a first direction transverse to the longitudinal axis of the capillary tube and a second direction along the longitudinal axis of the capillary tube.

10. A method as in claim 9 wherein optically scanning the sample in a first direction transverse to the longitudinal axis of the capillary tube comprises traversing a scan path that originates and terminates at points beyond respective outer boundaries of the capillary tube.

11. A method as in claim 1 wherein optically scanning the sample comprises scanning a capillary tube that is in a fixed position.

12. A method as in claim 1 further comprising determining a concentration of a cellular component of the sample by calculating an amount of enumerated component per specified volume of the capillary tube, the volume being determined by origination and termination points of a scan in a direction along the longitudinal axis of the capillary tube and a cross-sectional area of the capillary tube.

13. A method as in claim 1 further comprising determining ratios of different cellular components of the sample by calculating an amount of each enumerated component and comparing relative amounts of each enumerated component.

14. An assay for identifying and enumerating leukocyte subclasses in whole blood via fluorescence, the assay comprising;

obtaining a sample of whole uncoagulated blood;

incubating the sample with an excess amount of a fluorescently-labeled antibody directed to specific cell surface markers of a leukocyte subclass within the sample to form fluorescent complexes;

placing the sample into a capillary tube having specified dimensions;

optically scanning the sample with an incident beam of light having a wavelength selected to excite the fluorescent complexes and to minimize interference from red blood cells present in the sample, the incident beam sequentially intersecting the capillary tube in a plurality of beam spots of specified diameter to illuminate a plurality of columnar regions;

sequentially detecting emitted fluorescence confined to an interior depth dimension of each columnar region;

recording the emitted fluorescence from each columnar region of heightened fluorescence intensity; and enumerating a subclass of leukocytes by determining a presence of the subclass in the sample from the emitted fluorescence.

15. An assay as in claim 14, further comprising diluting the sample after said incubating step and prior to said placing the sample into a capillary tube step.

16. An assay as in claim 14 wherein incubating the sample with a fluorescently-labeled antibody comprises incubating with a plurality of fluorescently-labeled antibodies, each antibody directed to a different specific cell surface marker of a leukocyte subclass, and each antibody labeled with a different fluorophore having different optical characteristics.

17. A scanning imaging cytometer for non-flowing fluids in a capillary tube, the cytometer comprising:

a transparent capillary tube containing a non-flowing fluid having complexes of cells and fluorescently-labeled binding agent in suspension with free fluorescently-labeled binding agent, said capillary tube having outer and inner walls;

a beam of light impinging upon the outer wall of said capillary tube transverse to a longitudinal axis of said capillary tube in a beam spot having a first diameter illuminating a columnar region of the fluid, said beam of light having an excitation wavelength for stimulating fluorescent emission from the complexes and the free binding agent;

a light detector spaced apart from said capillary tube and responsive to the fluorescent emission;

a wide angle light collector positioned proximate said capillary tube, said light collector configured to gather fluorescent emission from the illuminated columnar region and to transmit the fluorescent emission towards said light detector in a retrobeam;

a spatial filter having a pinhole aperture, said spatial filter positioned between said light collector and said detector, the pinhole aperture disposed to intercept the retrobeam and having a second diameter admitting only a portion of the retrobeam to said detector, the second diameter of the pinhole aperture substantially exceeding the first diameter of the beam spot, so as to confine a depth of detection to an interior depth dimension of said capillary tube; and means for providing motion of said beam of light relative to said capillary tube to cause said beam of light to sequentially impinge upon said capillary tube in a plurality of beam spots, so as to illuminate within the capillary tube a plurality of columnar regions whose total volume can be determined.

18. A scanning imaging cytometer as in claim 17 wherein the fluorescently-labeled binding agent contains a fluorophore that is activated at an excitation wavelength in the range of 600 to 1000 nanometers.

19. A scanning imaging cytometer as in claim 17 wherein the binding agent is an antibody.

20. A scanning imaging cytometer as in claim 17 wherein the binding agent is specific to cell surface markers.

21. A scanning imaging cytometer as in claim 17 wherein the binding agent is an intercalating dye.

22. A scanning imaging cytometer as in claim 17 wherein the binding agent is a nucleic acid probe.

23. A scanning imaging cytometer as in claim 17 wherein the binding agent reacts with specific receptors.

24. A scanning imaging cytometer as in claim 17 wherein the beam of light impinging upon the outer wall of the capillary tube passes through a central portion of the wide angle light collector and then impinges on the outer wall of the capillary tube and is focused into an interior depth of the capillary tube.

25. A scanning imaging cytometer as in claim 17 further comprising particle counting means associated with the detector for distinguishing background fluorescence associated with free binding agent from fluorescence associated with complexes.

26. A scanning imaging cytometer as in claim 17 wherein the means for providing motion causes the plurality of spots to partially overlap each other.

27. A scanning imaging cytometer as in claim 17 wherein the means for providing motion causes the said beam of light to overscan lateral edges of the capillary tube.

28. A scanning imaging cytometer as in claim 17 wherein the means for providing motion causes the said beam of light to sequentially impinge upon the capillary tube in a two-dimensional array of spots, illuminating a two-dimensional array of columnar regions whose total volume can be determined.

29. A scanning image cytometer as in claim 17, wherein said light detector comprises a spectral dispersion device positioned between said spatial filter and first and second light sensitive members, the spectral dispersion device configured for separating a plurality of fluorescent emission wavelengths and directing the separated wavelengths to the first and second light sensitive members.

30. A scanning imaging cytometer as in claim 17 wherein the volume probed is determined by a known cross-sectional area of the capillary tube and a distance that has been scanned along the capillary tube.

31. A scanning imaging cytometer as in claim 17 wherein the volume is determined by a known cross-sectional area of the capillary tube and by providing specific identification marks on the capillary tube to define distance.

32. A scanning imaging cytometer as in claim 17 wherein the beam is focused to a location within the capillary tube.

33. A scanning imaging cytometer as in claim 17 wherein the beam of light has a wavelength in the range of 600 to 1000 nanometers.

34. A scanning imaging cytometer for non-flowing fluids in a capillary tube, the cytometer comprising:

a transparent capillary tube containing a non-flowing fluid having complexes of cells and fluorescently-labeled binding agent, the capillary having outer and inner walls;

a beam of light impinging upon the outer wall of said capillary tube transverse to a longitudinal axis of said capillary tube in a beam spot having a first diameter illuminating a columnar region of the fluid, said beam of light having an excitation wavelength for stimulating fluorescent emission from the complexes;

a light detector spaced apart from said capillary tube and responsive to the fluorescent emission;

a wide angle light collector positioned proximate said capillary tube, said light collector configured to gather fluorescent emission from the illuminated columnar region and to transmit the fluorescent emission towards said light detector in a retrobeam;

a spatial filter having a pinhole aperture, said spatial filter positioned between said light collector and said detector, the pinhole aperture disposed to intercept the retrobeam and having a second diameter admitting most of the retrobeam to said detector, the second diameter of the pinhole aperture substantially exceeding the first diameter of the beam spot, so as to confine a depth of detection to an interior depth dimension of said capillary tube; and means for providing motion of said beam of light relative to said capillary tube to cause said beam of light to sequentially impinge upon said capillary tube in a plurality of beam spots, so as to illuminate within the capillary tube a plurality of columnar regions whose total volume can be determined.

35. An apparatus for making volumetric fluorescence measurements of a cell suspension, the apparatus comprising:

a capillary tube of rectangular cross-section with a shorter dimension of the cross-section defining a depth of said capillary tube and a longer dimension of the cross-section defining a width of said capillary tube, said capillary tube containing a cell suspension therein;

optical scanning means for generating an incident beam of a wavelength selected to excite the cell suspension of the capillary tube, the incident beam sequentially intersecting the capillary tube in a plurality of beam spots of specified diameter to illuminate a plurality of columnar regions;

detection means having a light sensitive member for detection of fluorescent emission;

collection means for gathering of fluorescent emission from the columnar region and for directing the fluorescent emission to said detection means;

a spatial filter with a specified pinhole aperture for allowing detection of fluorescent light emitted from the entire columnar region, said spatial filter disposed between said collection means and said detection means, so as to confine a depth of detection to an interior depth dimension of said capillary tube; and a data reader in communication with said detection means for recordation of fluorescent emission signals.

36. An apparatus as in claim 35 wherein the capillary tube is positioned horizontally and the incident beam of the optical scanning means intersects the capillary tube from a position directly above the capillary tube.

37. An apparatus as in claim 35 wherein the wavelength of the incident beam is 600 to 1000 nanometers.

38. An apparatus as in claim 35 wherein the diameter of the beam spot is in the range of 5 to 15 microns.

39. An apparatus as in claim 35, wherein the capillary tube has a depth in the range of 25 to 225 microns.

40. An apparatus as in claim 35 wherein the incident beam of the optical scanning means traverses a path in a first direction along the width of the capillary tube and a second direction along a longitudinal axis of the capillary tube.

41. An apparatus as in claim 35 wherein the optical scanning means traverses a path in a direction along the width of the capillary tube and the path originates and terminates at points beyond the respective outer boundaries of the capillary tube.

42. An apparatus as in claim 35, wherein said detection means comprises a spectral dispersion device positioned between said spatial filter and first and second light sensitive members, the spectral dispersion device configured for separating a plurality of fluorescent emission wavelengths and directing the separated wavelengths to the first and second light sensitive members.

43. An apparatus as in claim 35 further comprising a lens, a central portion of the lens being used by the optical scanning means for passage of the incident beam before intersection of the incident beam with the capillary tube, and the entire lens being used by the collection means for gathering of fluorescent emission from the capillary tube.

44. An apparatus for the detection of subclasses of blood cells, the apparatus comprising:

a transparent capillary having a known rectangular cross-sectional area and having a known depth, thereby providing a known volume, wherein the depth substantially exceeds ten microns;

means for generating a beam of light having an excitation wavelength of at least 600 nanometers and configured to impinge upon the upper surface of said capillary so as to provide a beam spot having a diameter of at least five microns;

means for providing motion of the beam of light relative to said capillary for causing the beam of light to impinge upon said capillary in a plurality of beam spots so as to illuminate within the capillary tube a plurality of columnar regions of known volume;

a light collector positioned proximate said capillary and configured to gather a fluorescent emission caused by said means for generating a beam of light and further configured to transmit the fluorescent emission in a retrobeam;

a light detector responsive to the fluorescent emission, said detector being positioned away from said capillary and positioned to be impinged by the retrobeam from said light collector; and a spatial filter positioned between said light collector and said detector, the spatial filter disposed to intercept the retrobeam and configured to admit only a portion of the retrobeam to said detector so as to limit light detected to a single columnar region illuminated by a single beam spot and confined to an interior depth dimension of each columnar region.

45. The apparatus of claim 44, wherein the depth of said capillary is in the range of 25 to 225 microns.

46. The apparatus of claim 45, wherein the excitation wavelength of the beam of light from said means for generating is in the range of 600 to 1000 nanometers.

47. The apparatus of claim 46, wherein the beam spot has a diameter in the range of five to fifteen microns.

* * * * *